United States Patent [19]

Pagnucco et al.

[11] 4,041,147

[45] Aug. 9, 1977

[54] ANGIOTENSIN IRADIOIMMUNOASSAY

[75] Inventors: Rinaldo G. Pagnucco, Somerville, N.J.; Roberta J. Muse, Philadelphia, Pa.; Dasika R. Murty, North Brunswick, N.J.

[73] Assignee: E. R. Squibb & Sons, Inc., Princeton, N.J.

[21] Appl. No.: 709,674

[22] Filed: July 29, 1976

[51] Int. Cl.² .................. G01N 33/00; G21H 5/02
[52] U.S. Cl. .................. 195/103.5 A; 23/230 B; 424/12; 424/1
[58] Field of Search ............... 424/1, 1.5, 12; 195/103.5; 23/230 B

[56] References Cited

U.S. PATENT DOCUMENTS 3,592,888  7/1971  Wolf ........................... 424/1
3,843,775  10/1974  Wolf ........................... 424/1
3,899,298  8/1975  Szczesniak ................. 424/1 X

OTHER PUBLICATIONS

Croll et al., *New Techniques in Tumor Location and Radioimmunoassay*, John Wiley & Sons, New York, 1974, pp. 39-49.

*Primary Examiner*—Benjamin R. Padgett
*Assistant Examiner*—Christine M. Nucker
*Attorney, Agent, or Firm*—Lawrence S. Levinson; Merle J. Smith; Donald J. Barrack

[57] ABSTRACT

In a radioimmunoassay for the determination of plasma renin activity, the use of a tris-maleate buffer solution of about pH 7.4 in the incubation of plasma samples results in a high generation of angiotensin I and an improved test.

4 Claims, No Drawings

ANGIOTENSIN IRADIOIMMUNOASSAY

BACKGROUND OF THE INVENTION

The measurement of various body constituents by the use of radioimmunoassay techniques has achieved widespread acceptance in recent years. Exemplary of substances which can be measured by radioimmunoassay using currently available commercial kits are ACTH (adrenocorticotropin), aldosterone, angiotensin I, angiotensin II, barbiturates, cyclic AMP, cyclic GMP, digoxin, folic acid, FSH (follicle stimulating hormone), gastrin, HAA (hepatitis associated antigen), HGH (human growth hormone), insulin, TSH (thyroid stimulating hormone), thyroxine (T4), triiodothyronine (T3), and vitamin B12.

Radioimmunoassay tests require a specific antibody, a radioisotope-labeled (hereinafter referred to as "radiolabeled") antigen, a pure sample of the antigen to be measured to serve as a reference standard, and means for the separation of free antigen from antibody-bound antigen. Radioimmunoassays follow the basic principle of saturation analysis, i.e., competition between labeled and unlabeled antigen for a fixed number of antibody binding sites. The term "antigen", as used in the field of radioimmunoassays, may cover substances of limited antigenicity. In those cases where the substance to be measured is of limited antigenicity, the substance can be coupled with an agent which will increase its antigenicity.

When radiolabeled antigen, unlabeled antigen, and antibody are brought together, the amount of radiolabeled antigen bound to antibody and the amount of radiolabeled antigen remaining unbound (free) has a direct relationship to the amount of unlabeled antigen preset when a given amount of antibody is present. Thus, by using a constant amount of antibody and radiolabeled antigen, and using known concentrations of unlabeled antigen, a standard (calibration) curve can be plotted showing antigen concentration versus the amount of radiolabeled antigen bound or versus radiolabeled antigen unbound, or versus a ratio of the two measurements. The concentration of antigen in an unknown sample can be read from the standard curve by determining the amount of bound or free radiolabeled antigen (or ratio of the two measurements) resulting when the unknown sample is mixed with the amount of radiolabeled antigen and antibody used to prepare the curve.

One body constituent for which no direct radioimmunoassay procedure is available is renin. Renin is an enzyme that is synthesized, stored and released from granules contained in the juxtaglomerular apparatus of the kidney. It is generally accepted that the major physiological role of renin is to act as the primary stimulus for maintenance of body sodium balance. Plasma renin activity is increased when there is a decreased renal perfusion pressure, and when there is a decreased delivery of sodium and water to the distal tubule. Renin acts on substrate, angiotensinogen, an α-2-globulin produced by the liver, to form a decapeptide, angiotensin I. Angiotensin I is biologically inactive, and is converted to the biologically active octapeptide, angiotensin II, in the pulmonary circulation. Angiotensin II acts as a highly potent vasopressor, and stimulates the adrenal gland to produce aldosterone. Aldosterone promotes the reabsorption of sodium by the distal tubule, and when secreted in excessive amounts, results in hypertension.

Plasma renin assays are used as an adjunct in determining whether hypertension is due to primary aldosteronism or to renal vascular disease. The hypertensive patient that has plasma renin levels suppressed below normal, and has a high aldosterone secretion rate will usually be found to have adrenal hyperplasia or an adenoma of the zona glomerulosa of the adrenal gland. In patients with renal artery stenosis, the renal venous blood from the ischemic kidney may be found to have higher plasma renin levels than renal venous blood from the unaffected kidney.

As described above the determination of plasma renin activity is a valuable tool in a physician's diagnosis and differentiation of hypertensive disorders. Because purified renin is not available, the direct radioimmunoassay of renin is not possible. However, if it is assumed that the angiotensin I generated by a plasma substrate is proportional to the plasma renin activity of that substrate, it is possible to determine the plasma renin activity of a substrate by using radioimmunoassay procedures to determine the amount of angiotensin I generated by that substrate.

SUMMARY OF THE INVENTION

It is an object of this invention to provide a method for maximizing the generation of angiotensin I from angiotensinogen by the action of the enzyme renin.

It is an object of this invention to provide an improved radioimmunoassay procedure for the measurement of angiotensin I.

These and other objects which will be apparent to the practitioner of this invention are realized by the incubation of a plasma substrate in a tris-maleate buffer solution of about pH 7.4.

Detailed Description of the Invention

In the determination of plasma renin activity by the radioimmunoassay of angiotensin I, the following reactions are critical:

(1) angiotensinogen 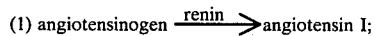 $\xrightarrow{\text{renin}}$ angiotensin I;

(2) angiotensin I 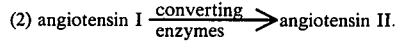 $\xrightarrow[\text{enzymes}]{\text{converting}}$ angiotensin II.

In order to achieve a consistent and accurate measure of angiotensin I it is necessary to maximize the generation of angiotensin I and inhibit its conversion to angiotensin II. The inhibition of the conversion of angiotensin I to angiotensin II is readily accomplished using one or more well known inhibitors; e.g., dimercaprol, 8-hydroxyquinoline sulfate, EDTA (edetic acid), diisopropylfluorophosphate, phenylmethylsulfonylfluoride and others. Maximizing the generation of angiotensin I by the action of renin on angiotensinogen has long been a goal of workers in this field. It has been disclosed that in the determination of angiotensin I by radioimmunoassay it is essential to control the pH of the enzymatic reaction which yields angiotensin I; see, for example, McDonald et al., *pH Dependence of the Renin Reaction*, Am. J. Clin. Path., 59:858(1973). The same investigators reported the maximum generation of angiotensin I occors at a pH of about 5.5. Generation of angiotensin I at a pH of about 5.5 was reported as 2-3 times greater than the generation at physiological pH (about 7.4).

Several investigators, while acknowledging the higher rate of generation of angiotensin I from angiotensinogen at pH 5.5, have reported that the generation is "non-specific"; see, for example, Oparil et al., *Effects of pH and Enzyme Inhibitors on Apparent Generation of Angiotensin I in Human Plasma,* J. Clin. Endocrinol. Metab., 39:965(1974). By "non-specific" generation is meant generation attributable to non-specific peptidases that are activated at the 5.5 pH. This theory has been disputed by proponents of pH 5.5 for maximum generation of angiotensin I.

It has now been found that the generation of angiotensin I from angiotensinogen at about pH 7.4 can be dramatically increased by the use of a buffer made up of about equimolar amounts of tris (hydroxymethyl-)aminomethane and maleic acid and adjusted to pH 7.4 with base; the buffer is referred to herein as tris-maleate buffer. The tris-maleate buffer is preferably used as an aqueous solution. Exemplary of the bases which can be used to adjust the pH to 7.4 are alkali metal hydroxides such as sodium hydroxide and potassium hydroxide. Surprisingly, the generation of angiotensin I at pH 7.4 in the presence of tris-maleate buffer is comparable to the generation of angiotensin I at pH 5.5–6.0.

Preparation of the tris-maleate buffer is readily accomplished by weighing out approximately equimolar amounts of tris (hydroxymethyl)aminomethane and maleic acid, adding water, and dissolving the solids by mixing at room temperature or at an elevated temperature. The pH adjustment of the buffer is conveniently accomplished by the addition of an appropriate amount of an aqueous solution of base.

Tris-maleate buffer at a pH of about 7.4 can be used to improve any assay which requires the generation of angiotensin I from angiotensinogen by the action of renin. The following description of a radioimmunoassay for angiotensin I is one such assay. Other assays which are well known in the art, can also be improved by the use of tris-maleate buffer.

The basic steps for the determination of angiotensin I concentration by radioimmunoassay can be described as follows:

1. Incubate part of a plasma sample containing an unknown concentration of angiotensin I at 37° C in a tris-maleate buffer solution of pH about 7.4 to generate angiotensin I from the angiotensinogen in the plasma sample and incubate part of the sample at 4° C without the addition of buffer.
2. Add a fixed amount of radiolabeled angiotensin I to a series of test tubes.
3. To two of the test tubes (all assays are preferably run in duplicate) add the 4° C incubated sample of plasma and to two other tubes add the 37° C incubated sample. To the other test tubes add known amounts of angiotensin I.
4. To each of the test tubes add a fixed amount of angiotensin I antiserum and incubate at 4° C.
5. Separate the bound radiolabeled angiotensin I from the free radiolabeled angiotensin I, and count either or both.
6. Reference (i) the amount of bound radiolabeled angiotensin I, (ii) the amount of free radiolabeled angiotensin I, or (iii) the ratio of bound/free or free/bound radiolabeled angiotensin I to the known amounts of unlabeled angiotensin I.
7. Using the relationship established in (6), determine the concentration of angiotensin I in the plasma sample.

The plasma sample should be collected in a cold tube containing an inhibitor to prevent the conversion of angiotensin I to angiotensin II. Part of the plasma sample is incubated at about 37° C in the tris-maleate buffer at about pH 7.4. This sample will reflect the quantity of angiotensin I generated through the action of renin in the plasma sample plus circulating levels of angiotensin I. An equal part of the plasma sample is incubated at 4° C without the addition of a buffer. This sample will reflect circulating levels of angiotensin I. The net quantity of angiotensin I generated at 37° C is calculated by subtracting the angiotensin I level in the 4° C sample from angiotensin I level in the 37° C sample. The presently preferred incubation time for both samples is two hours, but other times may be used since results are reported as a function of time.

The radiolabeled angiotensin I referred to above may utilize any one of many radioisotopes as the labeling material. The art has found that iodine-125 and iodine-131 are particularly useful because of their radiation energies. Iodine-125 is most preferred because of its longer half-life. Radiolabeled angiotensin I is a commercially available material.

Angiotensin I antiserum can be obtained using any one of the many procedures known in the art; see, for example, Haber et al., *Application of Radioimmunoassay for Angiotensin I to the Physiologic Measurements of Plasma Renin Activity in Normal Human Subjects,* J. Clin. Endocr. 29:1349(1969). Although antibodies obtained from the blood serum of research animals are generally acceptable for use in the radioimmunoassay of angiotensin I, antibodies obtained from rabbits injected with angiotensin I poly-L-lysine or angiotensin I thyroglobulin conjugate have been found to be particularly useful.

Many procedures for separating bound from free radiolabeled angiotensin I are known to a person of ordinary skill in the art. Exemplary of these procedures is the use of a suspension of powdered charcoal (see U.S. Pat. No. 3,899,298), a suspension of powdered charcoal coated with dextran (see U.S. Pat. No. 3,843,775), paper radioelectrophoresis (see U.S. Pat. No. 3,843,775) and ion exchange resins (see U.S. Pat. No. 3,843,775). It has been found particularly useful to use charcoal in tablet form as the means for separating bound from free radiolabeled angiotensin I.

What is claimed is:

1. A process for maximizing the generation of angiotensin I from angiotensinogen which comprises incubating the angiotensinogen substrate in a buffer solution of pH about 7.4, said buffer comprising about equimolar amounts of tris (hydroxymethyl)aminomethane and maleic acid.

2. A process in accordance with claim 1 wherein the angiotensinogen substrate is incubated at a temperature of about 37° C.

3. A process in accordance with claim 1 wherein the angiotensinogen substrate is incubated for about 2 hours.

4. In a radioimmunoassay for the determination of angiotensin I in a plasma sample which comprises (i) incubating the plasma sample to generate angiotensin I from angiotensinogen, (ii) forming a mixture of the incubated sample, radioisotope-labeled angiotensin I, and angiotensin I antiserum, (iii) separating the radioisotope-labeled angiotensin I bound to the angiotensin I antiserum from the free radioisotope-labeled angiotensin I, (iv) determining the radioactivity of the bound radioisotope-labeled angiotensin I, the radioactivity of the free radioisotope-labeled angiotensin I, or the radioactivity of each, (v) referencing the amount of bound radioisotope-labeled angiotensin I, the amount of free radioisotope-labeled angiotensin I, or the ratio of bound/free or free/bound radioisotope-labeled angiotensin I to corresponding values obtained by carrying out steps (ii), (iii) and (iv) using as a sample known amounts of angiotensin I, and (vi) determining the amount of angiotensin I in the plasma sample using the relationship established in (v), the improvement comprising: incubating the plasma sample in a buffer solution of pH about 7.4, said buffer comprising about equimolar amounts of tris (hydroxymethyl) aminomethane and maleic acid.

* * * * *